United States Patent [19]

Atwal

[11] Patent Number: 4,689,414
[45] Date of Patent: Aug. 25, 1987

[54] 2-(SUBSTITUTED IMINO)-6-ARYL-3,6-DIHYDRO-4-SUBSTITUTED-1,5(2H)-PYRIMIDINECARBOXYLIC ACIDS AND ANALOGS

[75] Inventor: Karnail Atwal, Cranbury, N.J.

[73] Assignee: E. R. Squibb & Sons, Inc., Princeton, N.J.

[21] Appl. No.: 832,184

[22] Filed: Feb. 24, 1986

[51] Int. Cl.$^4$ .......................................... C07D 239/22
[52] U.S. Cl. ..................... 544/297; 544/295;
544/296; 544/331; 544/332; 544/2; 544/3;
544/5; 544/7; 544/8; 544/55; 544/58.1;
544/58.5; 544/58.6; 544/63; 544/65; 544/66;
544/67; 544/72; 544/82; 544/96; 544/111;
544/112; 544/113; 544/114; 544/120; 544/121;
544/122; 544/123; 544/179; 544/180; 544/182;
544/238
[58] Field of Search ............... 544/297, 331, 332

[56] References Cited

U.S. PATENT DOCUMENTS 4,532,248 7/1985 Franckowiak et al. ............. 514/302

OTHER PUBLICATIONS

*J. Org. Chem.*, vol. 50, pp. 4227–4230, "Synthesis of Novel Dihydropyrimidines and Tetrahydropyrimidines", Cho et al., (1985).
*Medicinal Chemistry*, Burger edit., 2nd ed., 1960, pp. 565–571, 579–581, and 600–601.
Hof, J. Cardiovas. Pharmacol., 6, pp. 399–406 (1984).
Hof, J. Cardiovas. Pharmacol., 6, pp. 407–416 (1984).

*Primary Examiner*—Alan L. Rotman
*Assistant Examiner*—Kurt G. Briscoe
*Attorney, Agent, or Firm*—Lawrence S. Levinson; Donald J. Barrack

[57] ABSTRACT

Cardiovascular activity is exhibited by compounds having the formula

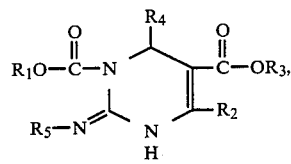

and pharmaceutically acceptable salts thereof, wherein $R_1$ is alkyl, cycloalkyl, aryl, heterocyclo, —(CH$_2$)$_n$—Y$_2$, —(CH$_2$)$_p$—Y$_3$ or halo substituted alkyl;
$R_2$ is hydrogen, alkyl, alkenyl, alkynyl, cycloalkyl, aryl, —(CH$_2$)$_n$—Y$_1$, or halo substituted alkyl;
$R_3$ is hydrogen, alkyl, cycloalkyl, aryl, heterocyclo, —(CH$_2$)$_n$—Y$_2$, —(CH$_2$)$_p$—Y$_3$, or halo substituted alkyl;
$R_4$ is aryl or heterocyclo;
$R_5$ is hydrogen, alkyl, aryl, arylalkyl, cyano, nitro,

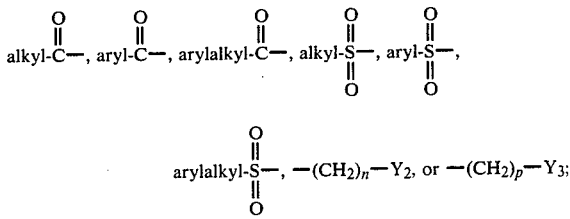

$Y_1$ is cycloalkyl, aryl, heterocyclo, hydroxyl, alkoxy, aryl-(CH$_2$)$_m$—O—, mercapto, alkylthio, aryl-(CH$_2$)$_m$—S—, amino, substituted amino, carbamoyl,

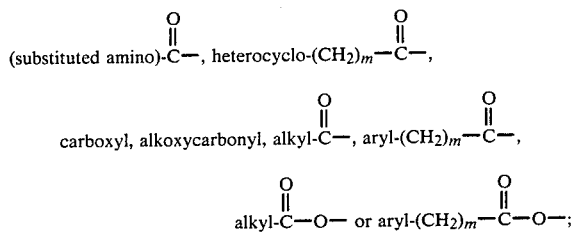

$Y_2$ is cycloalkyl, aryl, heterocyclo, carbamoyl,

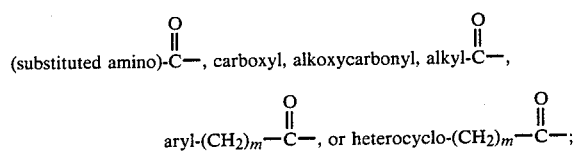

$Y_3$ is hydroxyl, alkoxy, aryl-(CH$_2$)$_m$—O—, mercapto, alkylthio,

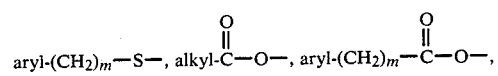

amino, or substituted amino;
m is 0 or an integer of 1 to 6;
n is an integer of 1 to 6; and
p is an integer of 2 to 6.

22 Claims, No Drawings

2-(SUBSTITUTED IMINO)-6-ARYL-3,6-DIHYDRO-4-SUBSTITUTED-1,5(2H)-PYRIMIDINECARBOXYLIC ACIDS AND ANALOGS

BRIEF DESCRIPTION OF THE INVENTION

Compounds having the formula $$R_1O-\overset{O}{\overset{\|}{C}}-N \begin{array}{c} R_4 \\ | \\ \end{array} \overset{O}{\overset{\|}{C}}-OR_3,$$

$$R_5-N \diagdown \diagup N \diagdown R_2$$
$$\qquad\quad H$$

and pharmaceutically acceptable salts thereof, are cardiovascular agents. In formula I, and throughout the specification, the symbols are as defined below.

$R_1$ is alkyl, cycloalkyl, aryl, heterocyclo, $-(CH_2)_n-Y_2$, $-(CH_2)_p-Y_3$ or halo substituted alkyl;

$R_2$ is hydrogen, alkyl, alkenyl, alkynyl, cycloalkyl, aryl, $-(CH_2)_n-Y_1$, or halo substituted alkyl;

$R_3$ is hydrogen, alkyl, cycloalkyl, aryl, heterocyclo, $-(CH_2)_n-Y_2$, $-(CH_2)_p-Y_3$, or halo substituted alkyl;

$R_4$ is aryl or heterocyclo;

$R_5$ is hydrogen, alkyl, aryl, arylalkyl, cyano, nitro, $$\text{alkyl-}\overset{O}{\overset{\|}{C}}-, \text{ aryl-}\overset{O}{\overset{\|}{C}}-, \text{ arylalkyl-}\overset{O}{\overset{\|}{C}}-, \text{ alkyl-}\overset{O}{\overset{\|}{\underset{\|}{S}}}-, \text{ aryl-}\overset{O}{\overset{\|}{\underset{\|}{S}}}-,$$
$$\qquad\qquad\qquad\qquad\qquad\qquad\qquad O \qquad\quad O$$

$$\text{arylalkyl-}\overset{O}{\overset{\|}{\underset{\|}{S}}}-, -(CH_2)_n-Y_2, \text{ or } -(CH_2)_p-Y_3;$$
$$\qquad O$$

$Y_1$ is cycloalkyl, aryl, heterocyclo, hydroxyl, alkoxy, aryl-$(CH_2)_m$—O—, mercapto, alkylthio, aryl-$(CH_2)_m$—S—, amino, substituted amino, carbamoyl, $$\text{(substituted amino)-}\overset{O}{\overset{\|}{C}}-, \text{ heterocyclo-}(CH_2)_m-\overset{O}{\overset{\|}{C}}-,$$

carboxyl, alkoxycarbonyl, alkyl-$\overset{O}{\overset{\|}{C}}$—, aryl-$(CH_2)_m$—$\overset{O}{\overset{\|}{C}}$—, alkyl-$\overset{O}{\overset{\|}{C}}$—O— or aryl-$(CH_2)_m$—$\overset{O}{\overset{\|}{C}}$—O—;

$Y_2$ is cycloalkyl, aryl, heterocyclo, carbamoyl, (substituted amino)—$\overset{O}{\overset{\|}{C}}$—, carboxyl, alkoxycarbonyl, alkyl—$\overset{O}{\overset{\|}{C}}$—, aryl—$(CH_2)_m$—$\overset{O}{\overset{\|}{C}}$—, or heterocyclo—$(CH_2)_m$—$\overset{O}{\overset{\|}{C}}$—;

$Y_3$ is hydroxyl, alkoxy, aryl-$(CH_2)_m$—O—, mercapto, alkylthio, aryl-$(CH_2)_m$—S—, alkyl—$\overset{O}{\overset{\|}{C}}$—O—, aryl—$(CH_2)_m$—$\overset{O}{\overset{\|}{C}}$—O—, amino, or substituted amino;

m is 0 or an integer of 1 to 6;

n is an integer of 1 to 6; and p is an integer of 2 to 6.

Listed below are definitions of various terms used to describe the compounds of this invention. These definitions apply to the terms as they are used throughout the specification (unless they are otherwise limited in specific instances) either individually or as part of a larger group.

The terms "alkyl" and "alkoxy" refer to both straight and branched chain groups. Those groups having 1 to 8 carbon atoms are preferred.

The term "halo substituted alkyl" refers to alkyl groups (as described above) in which one or more hydrogens have been replaced by chloro, bromo or fluoro groups. Exemplary groups are trifluoromethyl, which is preferred, pentafluoroethyl, 2,2,2-trichloroethyl, chloromethyl, bromomethyl, etc.

The term "aryl" refers to phenyl and substituted phenyl. Exemplary substituted phenyl groups are phenyl groups substituted with one, two or three alkyl, alkoxy, alkylthio, halo, nitro, cyano, hydroxy, amino, alkylamino, dialkylamino, trifluoromethyl, isothiocyanato, isocyanato, or difluoromethoxy groups.

The terms "alkenyl" and "alkynyl" refer to both straight and branched chain groups. Those groups having 2 to 8 carbon atoms are preferred.

The term "cycloalkyl" refers to those groups having 3, 4, 5, 6 or 7 carbon atoms.

The term "halo" refers to chloro, bromo, fluoro and iodo.

The term "heterocyclo" refers to fully saturated or unsaturated rings of 5 or 6 atoms containing one or two oxygen or sulfur atoms and/or one to four nitrogen atoms provided that the total number of hetero atoms in the ring is 4 or less. The heterocyclo ring is attached by way of an available carbon atom. Preferred monocyclic heterocyclo groups include 2- and 3-thienyl, 2- and 3-furyl, 2- and 3-pyrrolyl, 2-, 3- and 4-pyridyl, 2-, 4- and 5-imidazolyl, 2- and 3-pyrrolidinyl, 2-, 3- and 4-piperidinyl, and 2-, 3- and 4-azepinyl. The term heterocyclo also includes bicyclic rings wherein the five or six membered ring containing oxygen, sulfur and nitrogen atoms as defined above is fused to a benzene ring and the bicyclic ring is attached by way of an available carbon atom in the benzene ring. Preferred bicyclic heterocyclo groups include 4, 5, 6 or 7-indolyl, 4, 5, 6 or 7-isoindolyl, 5, 6, 7 or 8-quinolinyl, 5, 6, 7 or 8-isoquinolinyl, 4, 5, 6 or 7-benzothiazolyl, 4, 5, 6 or 7-benzoxazolyl, 4, 5, 6 or 7-benzimidazolyl, 4, 5, 6 or 7-benzoxadiazolyl, and 4, 5, 6 or 7-benzofurazanyl.

The term heterocyclo also includes such monocyclic and bicyclic rings as defined above substituted with one, or more, alkyl, arylalkyl, diarylalkyl, alkylthio, alkoxy, halo, nitro, oxo, cyano, hydroxy, amino, alkylamino, dialkylamino, trifluoromethyl, isocyanato, isothiocyanato or difluoromethoxy groups.

The term "substituted amino" refers to a group of the formula $-NZ_1Z_2$ wherein $Z_1$ is hydrogen, alkyl, or aryl-$(CH_2)_m$— and $Z_2$ is alkyl or aryl-$(CH_2)_m$— or $Z_1$ and $Z_2$ taken together with the nitrogen atom to which they are attached are 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, or 1-pyrrolidinyl, 1-piperidinyl, or 1-azepinyl substituted with alkyl, alkoxy, alkylthio, halo, trifluoromethyl or hydroxy.

DETAILED DESCRIPTION OF THE INVENTION

The compounds of formula I, and the pharmaceutically acceptable salts thereof, are cardiovascular agents. They act as calcium entry blocking vasodilators and are especially useful as hypotensive agents. Thus, by the administration of a composition containing one (or a combination) of the compounds of this invention, the blood pressure of a hypertensive mammalian (e.g., human) host is reduced. A single dose, or preferably two to four divided daily doses, provided on a basis of about 0.1 to 100 mg per kilogram of body weight per day, preferably from about 1 to about 50 mg per kilogram per day, is appropriate to reduce blood pressure. The substance is preferably administered orally, but parenteral routes such as the subcutaneous, intramuscular or intravenous routes can also be employed.

As a result of the calcium entry blocking activity of the compounds of formula I, and the pharmaceutically acceptable salts thereof, it is believed that such compounds in addition to being hypotensive agents may also be useful as anti-arrhythmic agents, and anti-anginal agents, as anti-fibrillatory agents, as anti-asthmatic agents, and in limiting myocardial infarction.

The compounds of this invention can also be formulated in combination with a diuretic, or a beta-adrenergic agent, or angiotensin converting enzyme inhibitor. Suitable diuretics include the thiazide diuretics such as hydrochlorothiazide and bendroflumethiazide, suitable beta-adrenergic agents include nadolol, and suitable angiotensin converting enzyme inhibitors include captopril.

The compounds of formula I can be formulated for use in the reduction of blood pressure in compositions such as tablets, capsules or elixirs for oral administration, or in sterile solutions or suspensions for parenteral administration. About 10 to 500 mg of a compound of formula I is compounded with physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The compounds of formula I wherein $R_5$ is cyano or nitro can be prepared by reacting a keto ester compound having the formula

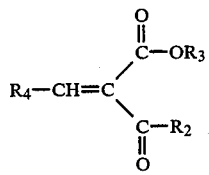

II with a compound having the formula

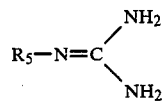

III to yield the corresponding compound having the formula

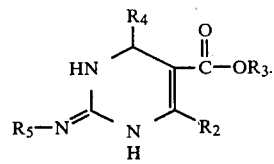

IV

The reaction proceeds most readily under reflux conditions.

Reaction of a compound of formula IV with an acyl chloride having the formula

V in the presence of an organic base yields the corresponding product of formula I.

The compounds of formula I wherein $R_5$ is hydrogen, alkyl, aryl, arylalkyl,

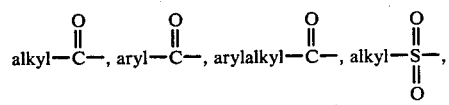

can be prepared by heating a keto ester of formula II with 2-methylpseudourea

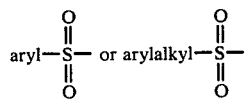

or a salt thereof, in the presence of sodium acetate or sodium bicarbonate to yield a compound having the formula

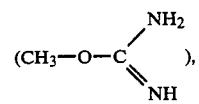

VI

Reaction of a compound of formula VI with an acyl chloride of formula V in the presence of an organic base yields the corresponding compound having the formula

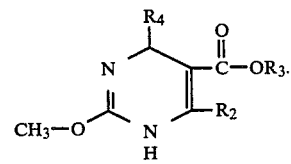

VII

A compound of formula VII can be converted to the corresponding product of formula I wherein $R_5$ is hydrogen by treatment with ammonia (preferably in the presence of an ammonium salt) or to the corresponding product of formula I wherein $R_5$ is alkyl, aryl, or arylalkyl by treatment with the appropriate amine having the formula $$R'_5-NH_2 \quad \text{VIII}$$

wherein $R'_5$ is alkyl, aryl or arylalkyl. The product of the above reactions have the formula $$R_1-O-\overset{\overset{O}{\|}}{C}-N\overset{R_4}{\underset{R''_5N}{\diagdown}}\overset{}{\underset{N}{\diagup}}\overset{\overset{O}{\|}}{C}-OR_3, \quad \text{IX}$$

wherein $R''_5$ is hydrogen, alkyl, aryl or arylalkyl.

Compounds of formula I wherein $R_5$ is an acyl or sulfonyl group can be prepared by acylation of the corresponding product of formula IX, wherein $R''_5$ is hydrogen, using conventional methodology.

The compounds of formula I form salts with a variety of inorganic and organic acids and bases. The pharmaceutically acceptable salts are preferred, although other salts may also be useful in isolating or purifying the product. Such pharmaceutically acceptable acid addition salts include those formed with hydrochloric acid, methanesulfonic acid, toluenesulfonic acid, sulfuric acid, acetic acid, maleic acid, etc. Pharmaceutically acceptable basic salts include alkali metal salts (e.g., sodium, potassium and lithium) and alkaline earth metal salts (e.g., calcium and magnesium).

Compounds of formula I exist as tautomeric mixtures. The two forms are shown below.

The tautomeric products are obtained in relative amounts that differ from compound to compound. Both forms are included within the scope of structural formula I.

Preferred compounds of this invention are those wherein:

$R_1$ is alkyl (especially ethyl);
$R_2$ is alkyl (especially methyl);
$R_3$ is alkyl (especially ethyl)
$R_4$ is aryl (especially 3-nitrophenyl and 2,3-dichlorophenyl); and
$R_5$ is hydrogen, cyano or nitro.

The following examples are specific embodiments of this invention.

EXAMPLE 1

2-(Cyanoimino)-6-(2,3-dichlorophenyl)-3,6-dihydro-4-methyl-1,5(2H)-pyrimidinedicarboxylic acid, 1-ethyl 5-methyl ester (A)

2-(Cyanoimino)-6-(2,3-dichlorophenyl)-3,6-dihydro-4-methyl-5-pyrimidinecarboxylic acid, methyl ester A reaction mixture containing 2-[(2,3-dichlorophenyl)methylene]-3-oxobutanoic acid, methyl ester (2.73 g, 10.0 mmoles) and cyanoguanidine (1.05 g, 12.5 mmoles) in dry pyridine (10 ml) was heated at reflux temperature for 24 hours. The reaction turned dark brown and some solid separated out. It was allowed to cool to ambient temperature and most of the pyridine was evaporated. The residue was triturated with ether and filtered to provide an off-white solid (2.1 g). This material was purified by flash chromatography (2-3% methanol in dichloromethane) and the resulting product was triturated with ethyl acetate-ether to provide colorless solid (470 mg), melting point >265° C. (dec). $R_f$ 0.27 on silica gel, ethyl acetate:dichloromethane (25:75).

(B)

2-(Cyanoimino)-6-(2,3-dichlorophenyl)-3,6-dihydro-4-methyl-1,5(2H)-pyrimidinedicarboxylic acid, 1-ethyl, 5-methyl ester A suspension of 2-(cyanoimino)-6-(2,3-dichlorophenyl)-3,6-dihydro-4-methyl-5-pyrimidinecarboxylic acid, methyl ester (444 mg, 1.31 mmoles) in dry dimethylformamide (2 ml) and tetrahydrofuran (2 ml) was cooled to 0° C. and was treated with triethylamine (0.5 ml) followed by ethyl chloroformate (284 mg, 2.62 mmoles). After the addition of ethyl chloroformate, the reaction turned yellow. The cooling bath was removed and stirring was continued at room temperature for 3 hours. The reaction was then diluted with ethyl acetate and washed with water, 5% citric acid, sodium bicarbonate and brine. After drying over magnesium sulfate, the solvent was evaporated and the residue was purified by flash chromatography (12% ethyl acetate in dichloromethane). The resulting product was crystallized from dichloromethane-isopropyl ether to provide 317 mg of the title compound as a colorless solid, melting point 176°–178° C.

Analysis Calc'd. for $C_{17}H_{16}Cl_2N_4O_4$:
C, 49.65; H, 3.92; N, 13.62; Cl, 17.24.
Found: C, 49.68; H, 3.90; N, 13.38; Cl, 17.39.

EXAMPLE 2

2-Amino-4-methyl-6-(3-nitrophenyl)-1,5(6H)-pyrimidinedicarboxylic acid, diethyl ester (A)

1,4-Dihydro-2-methoxy-6-methyl-4-(3-nitrophenyl)-5-pyrimidinecarboxylic acid, ethyl ester A reaction mixture containing 2-[(3-nitrophenyl)methylene]-3-oxobutanoic acid, ethyl ester (2.62 g, 10.0 mmole), 2-methylpseudourea sulfate (1.72 g, 10.0 mmole), and sodium bicarbonate (2.52 g, 30.0 mmole) in dimethylformamide (10 ml) was heated at 65°–70° C. for 16 hours. The reaction mixture was allowed to cool to room temperature, diluted with ethyl acetate, and filtered. The filtrate was washed with water and brine, and then dried over anhydrous magnesium sulfate. Evaporation of the solvent gave a yellow oil which was purified by flash chromatography (5% ethyl acetate in dichloromethane). The resulting foam was crystallized from isopropyl ether/hexanes to provide 2.41 g of 1,4-dihydro-2-methoxy-6-methyl-4-(3-nitrophenyl)-5-pyrimidinecarboxylic acid, ethyl ester as a colorless crystalline product; melting point 103.5°–105° C. TLC (silica gel; ethyl acetate: hexanes 50:50) $R_f$=0.31

Analysis Calc'd. for $C_{15}H_{17}N_3O_5$: C, 56.42; H, 5.37; N, 13.16;
Found: C, 56.52; H, 5.35; N, 13.03.

(B)
2-Methoxy-4-methyl-6-(3-nitrophenyl)-1,5(6H)-pyrimidinedicarboxylic acid, diethyl ester A solution of 1,4-dihydro-2-methoxy-6-methyl-4-(3-nitrophenyl)-5-pyrimidinecarboxylic acid, ethyl ester (3.19 g, 10.0 mmoles) in dry dichloromethane (15 ml) and pyridine (4 ml) was cooled to 0° C. and treated dropwise with ethyl chloroformate (1.2 ml, 12.0 mmoles) under argon. After the addition was completed, the cooling bath was removed and the reaction was allowed to stir at room temperature for 1 hour. It was then diluted with ethyl acetate and the resulting solution was washed with water, sodium bicarbonate and brine. After drying over anhydrous magnesium sulfate, the solvent was evaporated. The residue was coevaporated with toluene to remove residual pyridine. The colorless solid obtained was subjected to high vacuum and used in the next reaction without further purification (3.81 g). For analytical purposes, a small amount of the compound was recrystallized from ether-hexanes to provide colorless solid, melting point 61.5°–64.5° C.

(C)
2-Amino-4-methyl-6-(3-nitrophenyl)-1,5(6H)-pyrimidinedicarboxylic acid, diethyl ester A solution of 2-methoxy-4-methyl-6-(3-nitrophenyl)-1,5(6H)-pyrimidinedicarboxylic acid, diethyl ester (3.78 g, 9.66 mmoles of crude from previous reaction) in anhydrous tetrahydrofuran (20 ml) was cooled to 0° C. (ice bath) and a slow stream of ammonia gas was bubbled through it for approximately 5 minutes. Solid ammonium acetate (385 mg, 5.0 mmoles) was added and the reaction flask was tightly stoppered and allowed to stir at room temperature for 72 hours. A light yellow solid precipitated out of the reaction. Excess ammonia and tetrahydrofuran were evaporated and the residue was dissolved in methylene chloride. The insoluble material (ammonium acetate) was filtered off and the filtrate was concentrated. The residue was purified by flash chromatography (30% ethyl acetate in dichloromethane). The desired product was crystallized from dichloromethane-isopropyl ether to provide 2.03 g of the title compound as a yellow solid, melting point 166°–168° C.

Analysis Calc'd. for $C_{17}H_{20}N_4O_6$: C, 54.25; H, 5.36; N, 14.89;
Found: C, 54.19; H, 5.19; N, 14.84.

EXAMPLE 3
2-(Acetylamino)-3,6-dihydro-4-methyl-6-(3-nitrophenyl)-1,5(2H)-pyrimidinedicarboxylic acid, diethyl ester A suspension of 2-amino-4-methyl-6-(3-nitrophenyl)-1,5(6H)-pyrimidinedicarboxylic acid, diethyl ester (550 mg, 1.46 mmoles, see Example 2) in dichloromethane (5.0 ml) and pyridine (0.5 ml) was treated with acetic anhydride (0.3 ml) and the reaction was allowed to stir at room temperature for 1 hour. The colorless reaction mixture was diluted with ethyl acetate and was washed with 5% citric acid, sodium bicarbonate solution and brine. It was dried over anhydrous magnesium sulfate and evaporated to provide a colorless foam. Crystallization from ether-hexanes provided the title compound as a colorless solid, melting point 154.5°–156° C.

Analysis Calc'd. for $C_{19}H_{22}N_4O_7$: C, 54.54; H, 5.30; N, 13.39;
Found: C, 54.61; H, 5.40; N, 13.29.

EXAMPLE 4
3,6-Dihydro-4-methyl-2-[(methylsulfonyl)imino]-6-(3-nitrophenyl)-1,5(2H)-pyrimidinedicarboxylic acid, diethyl ester A suspension of 2-amino-4-methyl-6-(3-nitrophenyl)-1,5(6H)-pyrimidinedicarboxylic acid, diethyl ester (600 mg, 1.59 mmoles, see Example 2) in dichloromethane (5 ml) and pyridine (1.0 ml) was cooled to 0° C. under argon and was treated dropwise with methanesulfonyl chloride (0.42 ml, 5.26 mmoles). A catalytic amount of 4-dimethylamionpyridine was added and the reaction was allowed to warm to room temperature. After stirring overnight, the reaction was diluted with ethyl acetate and was washed with 1N hydrochloric acid, sodium bicarbonate and brine. It was dried over anhydrous magnesium sulfate and the solvent was evaporated to provide a colorless residue. Crystallization from ether-hexanes provided the title compound as a colorless crystalline material, melting point 139°–140.5° C.

Analysis Calc'd. for $C_{18}H_{22}N_4O_8S$: C, 47.57; H, 4.88; N, 12.33; S, 7.05;
Found: C, 47.52; H, 4.94; N, 12.17; S, 7.12.

EXAMPLE 5
3,6-Dihydro-2-cyanoimino-4-methyl-6-(3-nitrophenyl)-1,5(2H)-pyrimidinedicarboxylic acid, diethyl ester (A)
1,2,3,4-Tetrahydro-2-cyanoimino-6-methyl-4-(3-nitrophenyl)-5-pyrimidinecarboxylic acid, ethyl ester A suspension containing 2-[3-(nitrophenyl)methylene]-3-oxobutanoic acid, ethyl ester (2.5 g, 7.50 mmoles) and cyanoguanidine (0.75 g, 9.25 mmoles) in anhydrous pyridine (10 ml) was heated at reflux temperature for 24 hours. The reaction was allowed to cool to room temperature and most of the pyridine was evaporated under reduced pressure. The residue was triturated with dichloromethaneether to provide an off-white solid. This material was purified by flash chromatography (2% methanol in dichloromethane) and the resulting solid was triturated with acetonitrile to provide colorless product (630 mg). Recrystallization from acetonitrile gave the title compound in analytically pure form, melting point 250.5°–252° C.

(B)
3,6-Dihydro-2-cyanoimino-4-methyl-6-(3-nitrophenyl)-1,5(2H)-pyrimidinedicarboxylic acid, diethyl ester A suspension of 1,2,3,4-tetrahydro-2-cyanoimino-6-methyl-4-(3-nitrophenyl)-5-pyrimidinecarboxylic acid, ethyl ester (565 mg, 1.72 mmoles) in dry tetrahydrofuran (70 ml) and pyridine (2.0 ml) was cooled to 0° C. and treated with ethyl chloroformate (0.17 ml, 2.24 mmoles) dropwise under argon. After the addition was completed, the cooling bath was removed and the reaction was allowed to stir at room temperature for 13 hours. Dry dimethylformamide (2.0 ml) was added and the reaction suspension became a homogeneous solution. It was then treated with triethylamine (0.5 ml) followed by ethyl chloroformate (0.1 ml). The reaction was allowed to stir at room temperature for 1 hour and then diluted with ethyl acetate. It was washed with 1N hydrochloric acid, water, sodium bicarbonate solution and brine. After drying over anhydrous magnesium sulfate, the solvent was evaporated. The residue was purified by flash chromatography (10% ethyl acetate in dichloromethane) to provide a light yellow foam (585 mg). This material was combined with another batch of the same product and was crystallized from isopropyl ether-dichloromethane to yield the title compound, melting point 173.5°–175° C.

Analysis Calc'd. for $C_{18}H_{19}N_5O_6$: C, 53.86; H, 4.77; N, 17.45;

Found: C, 53.83; H, 4.87; N, 17.13.

EXAMPLE 6

3,6-Dihydro-4-methyl-2-(nitroimino)-6-(3-nitrophenyl)-1,5(2H)-pyrimidinedicarboxylic acid, diethyl ester (A)

1,2,3,4-Tetrahydro-6-methyl-2-(nitroimino)-4-(3-nitrophenyl)-5-pyrimidinecarboxylic acid A suspension containing 2-[3-(nitrophenyl)methylene]-3-oxobutanoic acid, ethyl ester (5.0 g, 19.0 mmoles) and nitroguanidine (3.42 g, 24.7 mmoles) in pyridine (20 ml) was heated at reflux temperature for 24 hours. The dark brown reaction was allowed to cool to room temperature and pyridine was evaporated. The residue was triturated with ether to provide yellow solid (5.3 g). This material was purified by flash chromatography (5% methanol in dichloromethane) and the resulting product was crystallized from acetonitrile to give the title compound as a yellow solid (1.1 g), melting point 236.5°–237.5° C. (with gas evolution).

(B)

3,6-Dihydro-4-methyl-2-(nitroimino)-6-(3-nitrophenyl)-1,5(2H)-pyrimidinecarboxylic acid, diethyl ester A solution of 1,2,3,4-tetrahydro-6-methyl-2-(nitroimino)-4-(3-nitrophenyl)-5-pyrimidinecarboxylic acid (700 mg, 2.0 mmoles) in tetrahydrofuran (10 ml) and dimethylformamide (2 ml) was allowed to cool to 0° C. and was treated dropwise under argon with ethyl chloroformate (0.25 ml, 2.6 mmoles). The reaction turned yellow and a colorless precipitate formed. The cooling bath was removed and the reaction was allowed to stir at room temperature for 2 hours; some unreacted starting material was still present. The reaction was diluted with ethyl acetate and was washed with water, 10% citric acid, sodium bicarbonate and brine. After drying over anhydrous magnesium sulfate, the solvent was evaporated. The residue was purified by flash chromatography (5% ethyl acetate in dichloromethane) and the product was crystallized from benzene-hexanes (cooling needed) to provide a colorless solid (350 mg). Recrystallization from ether-hexanes provided the analytically pure title compound, melting point 66°–69° C.

Analysis Calc'd. for $C_{17}H_{19}N_5O_8$: C, 48.46; H, 4.55, N, 16.62;

Found: C, 48.75; H, 4.69; N, 16.32.

EXAMPLE 7

4-Methyl-2-(methylamino)-6-(3-nitrophenyl)-1,5(6H)-pyrimidinedicarboxylic acid, diethyl ester (A)

2-Methoxy-4-methyl-6-(3-nitrophenyl)-1,5(6H)-pyrimidinedicarboxylic acid, diethyl ester A solution of 1,4-dihydro-2-methoxy-6-methyl-4-(3-nitrophenyl)-5-pyrimidinecarboxylic acid, ethyl ester (3.19 g, 10.0 mmoles) in dichloromethane (25 ml) and pyridine (5.0 ml) under argon was cooled to 0° C. and was treated dropwise with ethyl chloroformate (1.2 ml of 0.7%, 12.0 mmoles). After the addition was completed, the reaction was allowed to warm to room temperature and stirred for 1 hour. It was then diluted with ethyl acetate and the resulting solution was washed with water, sodium bicarbonate and brine. After drying over anhydrous magnesium sulfate, the solvent was evaporated to provide 2-methoxy-4-methyl-6-(3-nitrophenyl)-1,5(6H)-pyrimidinedicarboxylic acid, diethyl ester as a light yellow foam (3.71 g). This material was used in the next reaction without purification.

(B)

4-Methyl-2-(methylamino)-6-(3-nitrophenyl)-1,5(6H)-pyrimidinedicarboxylic acid, diethyl ester A solution of 2-methoxy-4-methyl-6-(3-nitrophenyl)-1,5(6H)-pyrimidinedicarboxylic acid, diethyl ester (3.71 g crude) in dimethylformamide (15 ml) was treated with methylamine hydrochloride (1.01 g, 15.0 mmoles) and sodium acetate (1.49 g, 17.0 mmoles). The reaction was allowed to stir at room temperature for 48 hours. It was then diluted with ethyl acetate and filtered. The filtrate was washed with water, sodium bicarbonate, brine and was dried over anhydrous magnesium sulfate. Solvent was evaporated under reduced pressure and the residue was purified by flash chromatography (5–7% ethyl acetate, dichloromethane). The product was crystallized from dichloromethane-isopropyl ether-hexanes to provide the title compound as yellow crystals (1.91 g), melting point 112.5°–114.5° C.

Analysis Calc'd. for $C_{18}H_{22}N_4O_6$: C, 55.38; H, 5.68; N, 14.35;

Found: C, 55.19; H, 5.59; N, 14.24.

Additional compounds falling within the scope of this invention are:

2-(cyanoimino)-6-(2,3-dichlorophenyl)-3,6-dihydro-4-methyl-1,5(2H)-pyrimidinecarboxylic acid, diethyl ester 6-(2,3-dichlorophenyl)-3,6-dihydro-4-methyl-2-(nitroimino)-1,5(2H)-pyrimidinecarboxylic acid, diethyl ester 2-(cyanoimino)-3,6-dihydro-4-methyl-6-(3-nitrophenyl)-1,5(2H)-pyrimidinecarboxylic acid, 1-[2-[(phenylmethyl)(methyl)amino]ethyl]5-(1-methylethyl) ester 3,6-dihydro-2-imino-4-methyl-6-(3-nitrophenyl)-1,5(2H)-pyrimidinecarboxylic acid, 1-(phenylmethyl) 5-(1-methylethyl) ester 2-(cyanoimino)-3,6-dihydro-4-methyl-6-(3-nitrophenyl)-1,5(2H)-pyrimidinecarboxylic acid, 1-(1-methylethyl) 5-2-[(phenylmethyl)(methyl)amino]ethyl]

2-(cyanoimino)-6-(2,3-dichlorophenyl)-3,6-dihydro-4-methyl-1,5(2H)-pyrimidinecarboxylic acid, 1-[2-(dimethylamino)ethyl] 5-ethyl ester 6-(2-chloro-3-nitrophenyl)-3,6-dihydro-2-imino-4-methyl-1,5(2H)-pyrimidinecarboxylic acid, 1-(1-methylethyl) 5-ethyl ester 3,6-dihydro-2-imino-4-methyl-6-[2-(trifluoromethyl)phenyl]-1,5(2H)-pyrimidinecarboxylic acid, 1-(1-methylethyl) 5-ethyl ester 2-(cyanoimino)-3,6-dihydro-4-methyl-6-(2-nitrophenyl)-1,5(2H)-pyrimidinecarboxylic acid, diethyl ester 3,6-dihydro-4-methyl-2-(nitroimino)-6-(3-nitrophenyl)-1,5(2H)-pyrimidinecarboxylic acid, 1-[1-(phenylmethyl)-4-piperidinyl] 5-ethyl ester

What is claimed is:

1. A compound having the formula

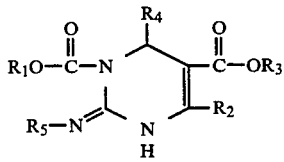

or a pharmaceutically acceptable salt thereof, wherein
$R_1$ is alkyl, cycloalkyl, aryl, $-(CH_2)_n-Y_2$, $-(CH_2)_p-Y_3$ or halo substituted alkyl;
$R_2$ is hydrogen, alkyl, alkenyl, alkynyl, cycloalkyl, aryl, $-(CH_2)_n-Y_1$, or halo substituted alkyl;
$R_3$ is hydrogen, alkyl, cycloalkyl, aryl, $-(CH_2)_n-Y_2$, $-(CH_2)_p-Y_3$, or halo substituted alkyl;
$R_4$ is aryl;
$R_5$ is hydrogen, alkyl, aryl, arylalkyl, cyano, nitro,

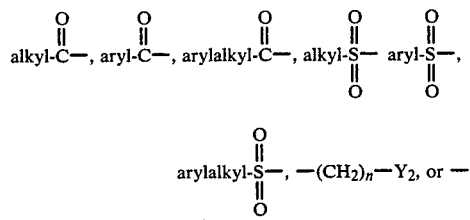

$Y_1$ is cycloalkyl, aryl, hydroxyl, alkoxy, aryl—$(CH_2)_m$—O—, mercapto, alkylthio, aryl—$(CH_2)_m$—S—, amino, substituted amino, carbamoyl,

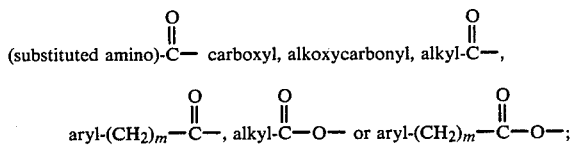

$Y_2$ is cycloalkyl, aryl, carbamoyl, (substituted amino)-C—,

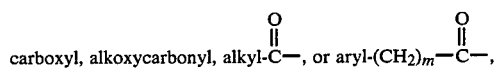

carboxyl, alkoxycarbonyl, alkyl-C—, or aryl-(CH_2)_m—C—, $Y_3$ is hydroxyl, alkoxy aryl—$(CH_2)_m$—O—, mercapto, alkylthio, aryl—$(CH_2)_m$—S—,

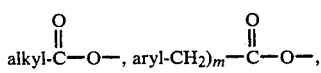

amino, or substituted amino;
m is 0 or an integer of 1 to 6;

n is an integer of 1 to 6; and
p is an integer of 2 to 6; wherein
the term "cycloalkyl" refers to cycloalkyl groups having 3, 4, 5, 6, or 7 carbon atoms;
the term "aryl" refers to phenyl and phenyl substituted with one, two or three alkyl, alkoxy, alkylthio, halo, nitro, cyano, hydroxy, amino, alkylamino, dialkylamino, trifluoromethyl, isothiocyanato, isocyanato, or difluoromethoxy groups; and
the term "substituted amino" refers to a group of the formula $-NZ_1Z_2$ wherein $Z_1$ hydrogen, alkyl, or aryl—$(CH_2)_m$— and $Z_2$ is alkyl or aryl—$(CH_2)_m$—.

2. A compound in accordance with claim 1 wherein $R_1$ is alkyl.

3. A compound in accordance with claim 2 wherein $R_1$ is ethyl.

4. A compound in accordance with claim 1 wherein $R_3$ is alkyl.

5. A compound in accordance with claim 4 wherein $R_3$ is ethyl.

6. A compound in accordance with claim 1 wherein $R_2$ is alkyl.

7. A compound in accordance with claim 6 wherein $R_2$ is methyl.

8. A compound in accordance with claim 1 wherein $R_4$ is aryl.

9. A compound in accordance with claim 8 wherein $R_4$ is 3-nitrophenyl.

10. A compound in accordance with claim 8 wherein $R_4$ is 2,3-dichlorophenyl.

11. A compound in accordance with claim 1 wherein $R_5$ is hydrogen.

12. A compound in accordance with claim 1 wherein $R_5$ is cyano.

13. A compound in accordance with claim 1 wherein $R_5$ is nitro.

14. A compound in accordance with claim 1 wherein $R_1$, $R_2$ and $R_3$ are each independently alkyl, $R_4$ is 3-nitrophenyl or 2,3-dichlorophenyl and $R_5$ is hydrogen, cyano or nitro.

15. A compound in accordance with claim 1 wherein $R_1$ and $R_3$ are each ethyl, $R_2$ is methyl, $R_4$ is 3-nitrophenyl or 2,3-dichlorophenyl and $R_5$ is hydrogen, cyano or nitro.

16. The compound in accordance with claim 1, 2-(cyanoimino)-6-(2,3-dichlorophenyl)-3,6-dihydro-4-methyl-1,5(2H)-pyrimidinedicarboxylic acid, 1-ethyl-5-methyl ester.

17. The compound in accordance with claim 1, 2-amino-4-methyl-6-(3-nitrophenyl)-1,5(6H)-pyrimidinedicarboxylic acid, diethyl ester.

18. The compound in accordance with claim 1, 2-(acetylamino)-3,6-dihydro-4-methyl-6-(3-nitrophenyl)-1,5(2H)-pyrimidinedicarboxylic acid, diethyl ester.

19. The compound in accordance with claim 1, 3,6-dihydro-4-methyl-2-[(methylsulfonyl)imino]-6-(3-nitrophenyl)-1,5(2H)-pyrimidinedicarboxylic acid, diethyl ester.

20. The compound in accordance with claim 1, 3,6-dihydro-2-cyanoimino-4-methyl-6-(3-nitrophenyl)-1,5(2H)-pyrimidinedicarboxylic acid, diethyl ester.

21. The compound in accordance with claim 1, 3,6-dihydro-4-methyl-2-(nitroimino)-6-(3-nitrophenyl)-1,5(2H)-pyrimidinedicarboxylic acid, diethyl ester.

22. The compound in accordance with claim 1, 4-methyl-2-(methylamino)-6-(3-nitrophenyl)-1,5(6H)pyrimidinedicarboxylic acid, diethyl ester.

* * * * *